(12) United States Patent
Muraoka et al.

(10) Patent No.: US 6,645,971 B1
(45) Date of Patent: Nov. 11, 2003

(54) QUINAZOLINONE DERIVATIVES

(75) Inventors: Masami Muraoka, Toyonaka (JP); Kazuki Matsui, Sanda (JP); Koji Morishita, Nishinomiya (JP); Naohito Ohashi, Takatsuki (JP)

(73) Assignee: Sumitomo Pharmaceuticals Company Limited, Osaka (JP)

( * ) Notice: Subject to any disclaimer, the term of this patent is extended or adjusted under 35 U.S.C. 154(b) by 0 days.

(21) Appl. No.: 09/807,173

(22) PCT Filed: Oct. 7, 1999

(86) PCT No.: PCT/JP99/05560

§ 371 (c)(1),
(2), (4) Date: Apr. 10, 2001

(87) PCT Pub. No.: WO00/23436

PCT Pub. Date: Apr. 27, 2000

(30) Foreign Application Priority Data

Oct. 16, 1998 (JP) .......................................... 10-295050

(51) Int. Cl.$^7$ ...................... A61K 31/517; A61K 31/52; A61P 13/10; C07D 413/00; C07D 401/00

(52) U.S. Cl. .............................. 514/266.22; 514/266.2; 514/266.23; 514/266.24; 514/266.3; 514/266.31; 514/258.1; 514/234.5; 514/252.04; 514/252.17; 544/116; 544/238; 544/253; 544/284; 544/286

(58) Field of Search ......................... 514/266.22, 266.3, 514/234.5, 252.04, 252.17, 266.2, 266.23, 266.24, 266.31, 258.1; 544/284, 286, 116, 238, 253

(56) References Cited

U.S. PATENT DOCUMENTS

| | | | |
|---|---|---|---|
| 3,547,921 A | | 12/1970 | Hardtmann et al. ......... 260/251 |
| 3,812,257 A | * | 5/1974 | Yamamoto et al. ....... 514/266.2 |
| 3,819,627 A | * | 6/1974 | Ott et al. .................... 544/286 |
| 3,829,420 A | | 8/1974 | Inaba et al. ................. 260/251 |
| 4,099,002 A | | 7/1978 | Inaba et al. ................. 260/251 |
| 5,556,860 A | * | 9/1996 | Muraoka et al. ....... 514/217.06 |

FOREIGN PATENT DOCUMENTS

| | | | |
|---|---|---|---|
| DE | 2162327 | * | 7/1972 |
| DE | 2307808 | * | 8/1973 |
| DE | 2166327 | * | 10/1973 |
| EP | 0 626 373 A1 | | 11/1994 |
| FR | 2 027 023 | | 9/1970 |
| FR | 2027023 | | 9/1970 |
| JP | 47-14183 | | 8/1972 |
| JP | 48-585 | | 1/1973 |
| JP | 48-22716 | | 7/1973 |
| JP | 48-34598 | | 10/1973 |
| JP | 49-25270 | | 6/1974 |
| JP | 07-41465 | | 2/1995 |

OTHER PUBLICATIONS

Patent Abstracts of Japan, 57095966, vol. 006, No. 180, 1982.
Patent Abstracts of Japan, 56113769, vol. 005, No. 194, 1981.
XP–000867004, M.J. Kornet et al., Synthesis of 3–Amino–3,4–dihydro–2(1H)–quinazolines as Potential Anticonvulsants, Journal of Heterocyclic Chemistry, vol. 21, 1984, p. 1709–1711.
Michihiro Yamamoto et al., "Synthetic Studies on Quinazoline Derivatives. II. The Reactions of 2–Trichloro–and 2–Trifluoroacetamidobenzophenones with Primary Amines", Chem. Pharm. Bull., vol. 29, No. 8, 1981, pp. 2135–2156.

* cited by examiner

Primary Examiner—Mukund J. Shah
Assistant Examiner—Tamthom N. Truong
(74) Attorney, Agent, or Firm—Sughrue Mion, PLLC

(57) ABSTRACT

A compound given by general formula (1):

(1)

[wherein T represents oxygen or sulfur atom, Y represents alkyl, cycloalkyl group, etc., ring W represents benzene ring, etc., $R^1$ and $R^2$ represent independently hydrogen atom, lower alkyl group, etc., and $R^3$ represents hydrogen atom, alkyl group, etc. Z represents a group given by formula:

{wherein $A^1$ and $A^2$ represent independently hydrogen atom, alkyl group, etc. and G represents straight chain alkylene having 1–6 of the carbon number, etc.} or a group given by formula:

{wherein n represents 0, 1 or 2, ring E represents 4–8 membered saturated heterocyclic ring containing nitrogen atom(s), and $A^3$ represents hydrogen atom, alkyl group, etc.}], its prodrug or pharmaceutically acceptable salt thereof is an antagonist against muscarinic receptor that is useful as anticholinergic medicaments, and therefore it is useful as pollakiuria or urinary incontinence remedy.

10 Claims, No Drawings

QUINAZOLINONE DERIVATIVES

This application is a national stage entry under 35 U.S.C. §371 of PCT/JP99/05560, filed on Oct. 7, 1999.

TECHNICAL FIELD

The present invention relates to a compound, which have antagonism effect on muscarinic receptor and can be useful as anticholinergic medicaments, its prodrug and pharmaceutically acceptable salt thereof, and their use. Antagonists against muscarinic receptor can be used, for example, as mydriatic medicament, anticonvulsant, parkinsonian remedy, antasthmatic, peptic ulcer remedy, secretagogue and motofacient for gastric and duodenal ulcer, intestinum hypersensitivity remedy, pollakiuria remedy, urinary incontinence remedy, antiarrhythmic medicament, esophageal achalasia remedy, chronic obstructive tracheal disease remedy and so on.

BACKGROUND ART

The quinazolinone derivatives having subneural, antiinflammatory and analgesic action are described in Japanese Unexanined Patent Publication No. sho47-14183, the quinazolinone derivatives having an effect of inhibiting central nervous system are described in French Patent No. 2,027,023, and the quinazolinone derivatives having an effect of preventing overload of calcium ions are described in Japanese Unexamined Patent Publication No. hei7-41465, respectively. However, they do not refer to the use of anticholinergic medicament, especially urinary incontinence and pollakiuria remedy.

DISCLOSURE OF THE INVENTION

The subject of the present invention is to provide antagonists against muscarinic receptor which is useful as anticholinergic medicament.

The present inventors have earnestly studied for solving the above problem, found that the compounds given by general formula (1) below, their prodrugs and pharmaceutically acceptable salts thereof have antagonism effect on muscarinic receptor, and now completed the present invention. Namely, the present invention relates to the following [11] to [15]:

[1] An anticholinergic medicament comprising a compound given by general formula (1):

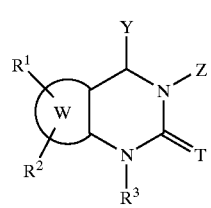

(1)

[wherein T represents oxygen or sulfur atom, and Y represents alkyl, cycloalkyl, cycloalkylalkyl, phenyl, substituted phenyl, aralkyl, substituted aralkyl, heteroaryl or substituted heteroaryl group. Ring W represents benzene, 5–6 membered heteroaromatic, 5–10 membered cycloalkene or 5–10 membered cycloalkane ring. $R^1$ and $R^2$ represent independently hydrogen atom, lower alkyl group, halogen atom, cyano, trifluoromethyl, nitro, amino, substituted amino, hydroxy, lower alkoxy, lower alkylthio, lower alkylsulfinyl or lower alkylsulfonyl group. $R^3$ represents hydrogen atom, alkyl, substituted alkyl, alkenyl, substituted alkenyl, alkynyl, substituted alkynyl, cycloalkyl, substituted cycloalkyl, cycloalkylalkyl, aralkyl or substituted aralkyl group.

Z represents a group given by formula:

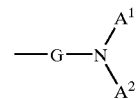

{wherein $A^1$ and $A_2$ represent independently hydrogen atom, alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —$CH_2R^4$ group (wherein $R^4$ represents alkenyl or alkynyl group), or $A^1$ and $A^2$ are combined together and form heterocyclic ring. G represents straight chain alkylene having 1–6 of the carbon number, branched alkylene having 2–8 of the carbon number, a group given by formula:

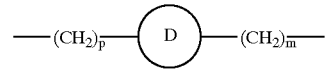

(wherein p and m represent independently 0, 1 or 2 and D represents cycloalkane ring)} or

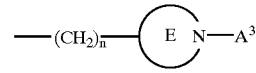

{wherein n represents 0, 1 or 2, ring E represents 4–8 membered saturated heterocyclic ring containing nitrogen atom(s), and $A^3$ represents hydrogen atom, alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —$CH_2R^4$ group (wherein $R^4$ represents alkenyl or alkynyl group), or forms bicyclo ring together with ring E}], its prodrug or pharmaceutically acceptable salt thereof as an active ingredient.

[2] An anticholinergic medicament described in [1], wherein ring W represents 5–6 membered heteroaromatic, 5–10 membered cycloalkene or 5–10 membered cycloalkane ring.

[3] An anticholinergic medicament described in [1], wherein ring W represents benzene ring and Z represents a group given by formula:

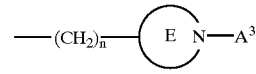

[4] An anticholinergic medicament described in [1], wherein Z represents a group given by formula:

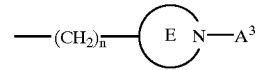

[5] An anticholinergic medicament described in [4], wherein ring W represents benzene or pyridine ring.

[6] An anticholinergic medicament described in [5], wherein ring W represents benzene ring.

[7] An anticholinergic medicament described in [6], wherein Y represents phenyl or substituted phenyl group.

[8] An anticholinergic medicament described in [4], wherein ring W represents benzene or pyridine ring and Z represents a group given by formula:

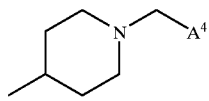

(wherein $A^4$ represents phenyl, substituted phenyl, cycloalkyl or cycloalkenyl group).

[9] An anticholinergic medicament described in [8], wherein $A^4$ represents cycloalkyl or cycloalkenyl group.

[10] An anticholinergic medicament described in [8], wherein $A^4$ represents phenyl or substituted phenyl group.

[11] An anticholinergic medicament described in [8], wherein $A^4$ represents substituted phenyl group and said substituent is cyano, alkoxyalkyl, alkanoylamino, aminocarbonyl, alkylaminocarbonyl or dialkylaminocarbonyl group.

[12] An anticholinergic medicament described in any of [1]–[11], wherein the medicament is urinary incontinence or pollakiuria remedy.

[13] A compound given by general formula (1):

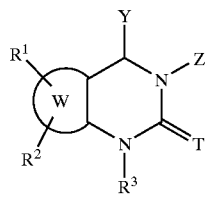

(1)

[wherein T represents oxygen or sulfur atom, and Y represents alkyl, cycloalkyl, cycloalkylalkyl, phenyl, substituted phenyl, aralkyl, substituted aralkyl, heteroaryl or substituted heteroaryl group. Ring W represents benzene or pyridine ring. $R^1$ and $R^2$ represent independently hydrogen atom, lower alkyl group, halogen atom, cyano, trifluoromethyl, nitro, amino, substituted amino, hydroxy, lower alkoxy, lower alkylthio, lower alkylsulfinyl or lower alkylsulfonyl group. $R^3$ represents hydrogen atom, alkyl, substituted alkyl, alkenyl, substituted alkenyl, alkynyl, substituted alkynyl, cycloalkyl, substituted cycloalkyl, aralkyl or substituted aralkyl group. Z represents a group given by formula:

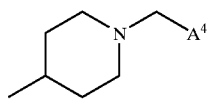

(wherein $A^4$ represents phenyl group substituted by alkoxyalkyl group), its prodrug or pharmaceutically acceptable salt thereof.

[14] A compound given by general formula (1a):

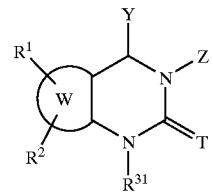

(1a)

[wherein T represents oxygen or sulfur atom, and Y represents alkyl, cycloalkyl, cycloalkylalkyl, phenyl, substituted phenyl, aralkyl, substituted aralkyl, heteroaryl or substituted heteroaryl group. Ring W represents benzene, 5–6 membered heteroaromatic, 5–10 membered cycloalkene or 5–10 membered cycloalkane ring. $R^1$ and $R^2$ represent independently hydrogen atom, lower alkyl group, halogen atom, cyano, trifluoromethyl, nitro, amino, substituted amino, hydroxy, lower alkoxy, lower alkylthio, lower alkylsulfinyl or lower alkylsulfonyl group. $R^{31}$ represents alkyl, substituted alkyl, alkenyl, substituted alkenyl, alkynyl, substituted alkynyl, cycloalkyl, substituted cycloalkyl, aralkyl or substituted aralkyl group. Z represents a group given by formula:

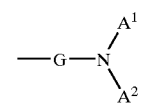

{wherein $A^1$ and $A^2$ represent independently hydrogen atom, alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —$CH_2R^4$ group (wherein $R^4$ represents alkenyl or alkynyl group), or $A^1$ and $A^2$ are combined together and form heterocyclic ring. G represents straight chain alkylene having 1–6 of the carbon number, branched alkylene having 1–8 of the carbon number, a group given by formula:

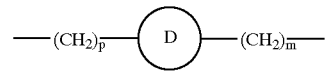

(wherein p and m represent independently 0, 1 or 2 and D represents cycloalkane ring)} or formula:

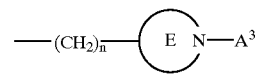

{wherein n represents 0, 1 or 2, ring E represents 4–8 membered saturated heterocyclic ring containing nitrogen atom(s), and $A^3$ represents hydrogen atom, alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —$CH_2R^4$ group (wherein $R^4$ represents alkenyl or alkynyl group), or forms bicyclo ring together with ring E}], its prodrug or pharmaceutically acceptable salt thereof

[15] A compound described in [14], wherein Z represents a group given by formula:

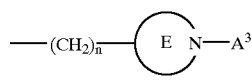

its prodrug or pharmaceutically acceptable salt thereof.

As the compounds given by general formula (1a) are a part of the compounds given by general formula (1), the explanation of the compounds given by general formula (1) should be construed as the explanation of the compounds given by general formula (1a).

Further, the compounds given by general formula (1), its prodrug or pharmaceutically acceptable salt thereof may be referred as to the present compound in this description.

A part of the compounds used in the present invention, namely, the presnt compounds, wherein ring W is benzene ring and Z is a group given by formula:

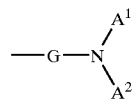

(wherein G, $A^1$ and $A^2$ mean as defined above) is known as compounds having subneural, anti-inflammatory and analgesic action in Japanese Unexamined Patent Publication No. sho47-14183, and compounds having an effect of inhibiting central nervous system in French Patent No. 2,027,023. Further, the present compounds, wherein $R^3$ is hydrogen atom, are known as medicament for preventing overload of calcium ions in Japanese Unexamined Patent Publication No. hei7-41465. However, in these publications, use of anticholinergic medicament, especially urinary incontinence and pollakiuria remedy is not described.

The various groups in the present invention are explained in detail below. The explanation for each group is also applied to the parts of the other substituents unless specifically noticed.

Typical 5–6 membered heteroaromatic ring for ring W is exemplified by heteroaromatic rings having 0, 1 or 2 nitrogen atom(s), 0 or 1 sulfur atom, and 0 or 1 oxygen atom. The examples are more typically as follows:

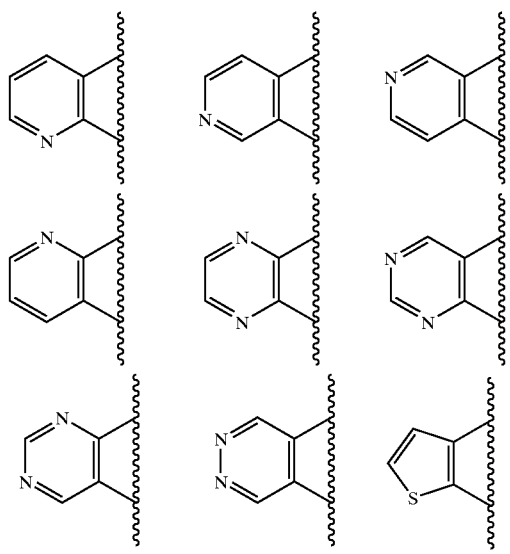

-continued

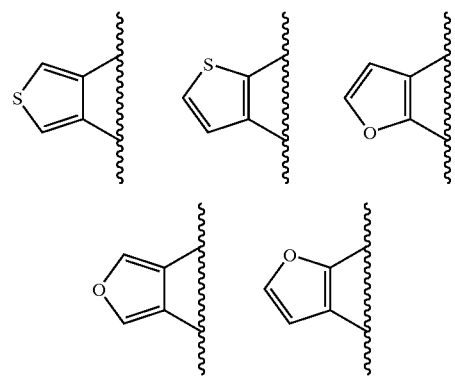

preferably the groups below:

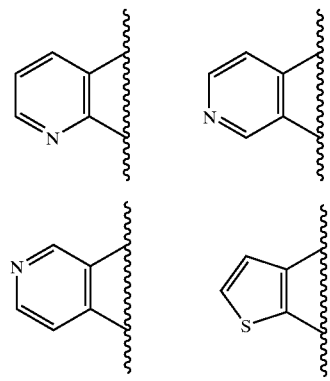

Typical 5–10 membered cycloalkene or cycloalkane ring for ring W is exemplified as follows:

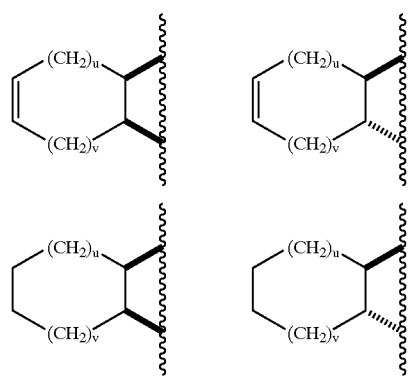

(wherein u and v independently represent 0 or an integer of 1 to 5, and u+v represents an integer of 1 to 6, further bold and dotted lines in the formulae represent relative configuration at adjacent carbon atoms of bridge head and do not represent a specific optical isomer, that is the same as the structural formulae hereinafter.), preferably the groups below:

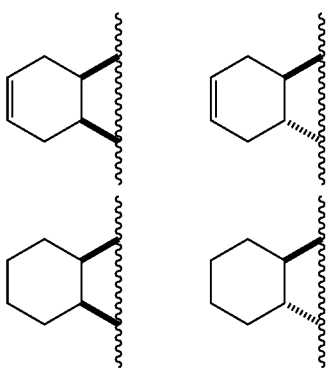

Typical straight chain alkylene having 1–6 of the carbon number for G is exemplified by methylene, dimethylene, trimethylene and tetramethylene, and typical branched alkylene having 2–8 of the carbon number is as follows:

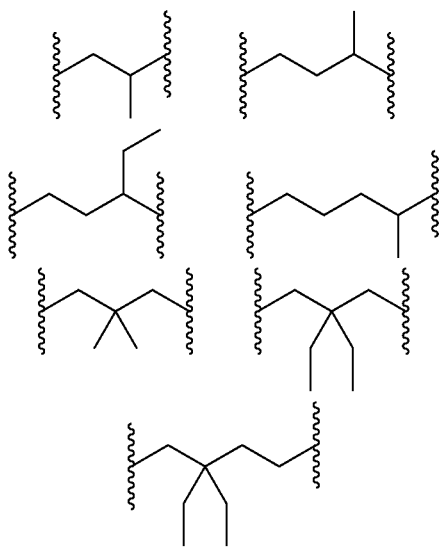

Examples of the cycloalkane ring for D include cycloalkane ring having 3–8 of the carbon number, typically cyclopropane, cyclobutane, cyclopentane, cyclohexane, cycloheptane and cyclooctane.

Preferable groups of G are exemplified by dimethylene, trimethylene, tetramethylene and the groups below:

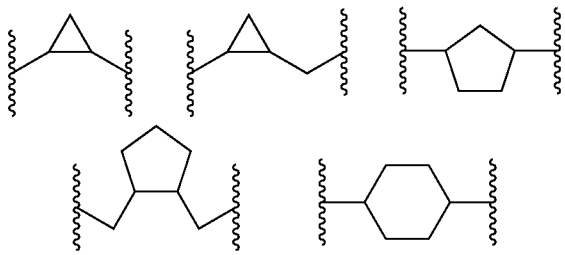

Examples of the alkyl group include straight chain or branched alkyl group having 1–8 of the carbon number, typically methyl, ethyl, propyl, 2-propyl, butyl, 2-butyl, 2-methylpropyl, 1,1-dimethylethyl, 3-pentyl, 3-hexyl, 4-heptyl and 4-octyl. Preferable group is exemplified by 2-propyl, butyl, 2-butyl, 2-methylpropyl, 3-pentyl and 3-hexyl for Y, and straight chain or branched alkyl group having 1–4 of the carbon number such as methyl, ethyl, propyl and 2-propyl for $A^1$ and $A^2$.

Examples of the acyl group include alkanoyl and aroyl group.

Examples of the alkanoyl group include one connected with alkyl group at either bond of the carbonyl group.

Examples of the aroyl group include one connected with aryl group at either bond of the carbonyl group.

Examples of the cycloalkyl group include cycloalkyl group having 3–8 carbon number, typically cyclopropyl, cyclobutyl, cyclopentyl, cyclohexyl, cycloheptyl and cyclooctyl.

Examples of the cycloalkylalkyl group include cycloalkylalkyl group having 10 or less of the carbon number, typically cyclopropylmethyl, 2-cyclopentylethyl, cyclohexylmethyl, 3-cyclohexylpropyl and 4-cyclohexylbutyl.

Examples of the cycloalkenylalkyl group include cycloalkenylalkyl group having 10 or less of the carbon number, typically 4-cyclohexenylmethyl, 4-cyclopentenylmethyl and 4-(4-cyclohexyenyl)butyl.

Examples of the alkenyl group include alkenyl group having 2–6 of the carbon number, typically vinyl, allyl, 1-propenyl, 1-butenyl, 2-pentenyl and 5-hexyenyl, preferably, allyl, 1-propenyl and 1-butenyl group.

Examples of the alkynyl group include alkynyl group having 2–6 of the carbon number, typically ethynyl, propargyl, 2-butynyl and 3-pentynyl, preferably ethynyl and propargyl.

Examples of the aralkyl group include aralkyl group having 12 or less of the carbon number, typically benzyl, 1-phenylethyl, 2-phenylethyl and 2-naphthylmethyl. Preferable group is benzyl group for $A^3$.

Examples of the heteroaryl group include 5–6 membered ring group containing 1 or 2 nitrogen atom(s), 5–6 membered ring group containing 1 or 2 nitrogen atom(s) and one oxygen or sulfur atom, and 5–6 membered ring group containing one oxygen or sulfur atom, typically 2-pyridyl, 3-pyridyl, 4-pyridyl, 2-thienyl, 3-oxadiazolyl, 2-imidazolyl, 2-thiazolyl, 3-isothiazolyl, 2-oxazolyl, 3-isoxazolyl, 2-furyl and 3-pyrrolyl.

Examples of the heteroaryl group for the heteroarylalkyl group include 5–6 membered ring group containing 1–4 nitrogen atom(s), and 5–6 membered ring group containing 1–2 nitrogen atom(s) and one oxygen or sulfur atom. Typical heteroarylalkyl group is exemplified by 2-pyridylmethyl, 3-pyridylmethyl, 4-pyridylmethyl, 1-(2-pyridyl)ethyl, 2-(2-pyridyl)ethyl, 2-thienylmethyl, 3-thienylmethyl, 3-oxadiazolylmethyl, 2-imidazolylmethyl, 2-thiazolylmethyl, 3-isothiazolylmethyl, 2-oxazolylmethyl, 3-isoxazolylmethyl, 2-furylmethyl, 3-furylmethyl and 2-pyrrolylmethyl.

Examples of the saturated heterocyclic group include the saturated heterocyclic group consisting of one hetero atom such as oxygen and sulfur atom and 3–5 carbon atoms, typically tetrahydropyran-4-yl, tetrahydrofuran-3-yl and tetrahydrothiophen-3-yl.

Examples of the heterocyclic ring formed by $A^1$ and $A^2$ bonded each other include 5–7 membered ring containing 1–2 nitrogen atom(s), or saturated or unsaturated 5–7 membered ring containing one nitrogen atom and one oxygen atom, typically pyrrolidine, piperidine, homopiperidine, piperazine, homopiperazine, morpholine, imidazole and pyrazole.

Examples of the 4–8 membered saturated heterocyclic ring containing nitrogen atom for ring E include ring containing 1 or 2 nitrogen atoms and 0 or 1 oxygen atom, typically pyrrolidin-2-yl, pyrrolidin-3-yl, piperidin-2-yl, piperidin-3-yl, piperidin-4-yl, homopiperidin-2-yl, homopiperidin-3-yl, homopiperidin-4-yl and morpholin-2-yl. When n is 0, piperidin-4-yl is preferable.

Examples of the bicyclo ring formed by ring E and $A^3$ include quinuclidin-3-yl and quinuclidin-4-yl.

Examples of the lower alkyl group include straight chain or branched alkyl group having 4 or less of the carbon number, typically methyl, ethyl, propyl, 2-propyl, butyl, 2-butyl, 2-methylpropyl and 1,1-dimethylethyl.

Examples of the halogen atom include fluorine, chlorine, bromine and iodine atom.

Examples of the lower alkoxy group include straight chain or branched alkoxy group having 4 or less of the carbon number, typically methoxy, ethoxy, propoxy, 2-propoxy, butoxy and 1,1-dimethylethoxy.

Examples of the lower alkylthio group include straight chain or branched alkylthio group having 4 or less of the carbon number, typically methylthio, ethylthio, 2-propylthio and butylthio.

Examples of the aryl group include the group having 10 or less of the carbon number, typically phenyl, 1-naphthyl and 2-naphthyl.

Examples of the lower alkylsulfinyl group include straight chain or branched alkylsulfinyl group having 4 or less of the carbon number, typically methylsulfinyl, ethylsulfinyl, propylsulfinyl, 2-propylsulfinyl and butylsulfinyl.

Examples of the lower alkylsulfonyl group include straight chain or branched alkylsulfonyl group having 4 or less of the carbon number, typically methylsulfonyl, ethylsulfonyl, propylsulfonyl, 2-propylsulfonyl and butylsulfonyl.

Examples of the substituent for the substituted amino group include alkyl or —$CH_2R^4$— group (wherein $R^4$ represents alkenyl or alkynyl group), and the substituent may be one or two which are the same or different from each other. Preferable substituted amino groups are exemplified by methylamino, ethylamino, allylamino, propargylamino, propylamino, 2-propylamino, butylamino, N,N-dimethylamino, N,N-diethylamino, N,N-dipropylamino and N,N-diallylamino.

Examples of the substituent for the substituted aryl, substituted phenyl, substituted aralkyl, substituted benzyl, substituted heteroaryl and substituted heteroarylalkyl group include lower alkyl, lower alkoxy, methylenedioxy group, halogen atom, cyano, trifluoromethyl, nitro, hydroxy, alkanoyloxy, carboxyl, alkoxycarbonyl, alkylthio, alkylsulfinyl, alkylsulfonyl, alkylsulfonamido group, a group of formula —$NR^6R^7$ (wherein $R^6$ and $R^7$ independently represent hydrogen atom, alkyl, —$CH_2R^4$ (wherein $R^4$ represents the meaning defined above), di- lower alkylamino-substituted alkyl, alkoxy-substituted alkyl, cycloalkyl, alkoxycarbonyl, heteroarylmethyl or aralkyl group, or $R^6$ and $R^7$ are combined together to form saturated cyclic amino group having 4 to 8 carbons, which constitute the ring, and further optionally one —$NR^8$— ($R^8$ represents hydrogen atom, lower alkyl, phenyl, lower alkoxycarbonyl or benzyl group) or one oxygen atom, with the nitrogen atom to which $R^6$ and $R^7$ are bonded), —C(=O)$NR^6R^7$ ($R^6$ and $R^7$ represent the same meanings defined above), —$NR^5$C(=O)$Q^1$ ($R^5$ represents hydrogen atom or lower alkyl group, and $Q^1$ represents alkyl, alkenyl, alkynyl, cycloalkyl, aryl, substituted aryl, aralkyl, substituted aralkyl, heteroaryl, substituted heteroaryl, heteroarylalkyl or substituted heteroarylalkyl group), or $E^1$—$M^1$—$E^2$—$Q^2$ {$E^1$ represents bond or divalent hydrocarbyl group having 1–4 of the carbon number, $M^1$ represents bond, oxygen or sulfur atom, or —$NR^5$— ($R^5$ represents the same meaning defined above). $E^2$ represents divalent hydrocarbyl group, which may contains unsaturated bond, having 1–6 of the carbon number, provided that $E^1$ and $M^1$ are combined to form one bond when both of $E^1$ and $M^1$ represent bond. $Q^2$ represents hydrogen atom, hydroxy, carboxyl, alkoxycarbonyl, alkanoyloxy, benzyloxycarbonyl group, halogen atom, cyano, benzyloxy, alkoxy, alkylthio, alkylsulfinyl, alkylsulfonyl, alkyl-substituted or unsubstituted benzene-sulfonyloxy (e.g. p-toluenesulfonyloxy), alkoxycarbonylamino, alkylsulfonamido, phthalimido, cycloalkyl, aryl, substituted aryl, heteroaryl, substituted heteroaryl group, a group of formula —$NR^6R^7$ ($R^6$ and $R^7$ represent the same meaning defined above), —C(=O)$NR^6R^7$ ($R^6$ and $R^7$ represent the same meanings defined above), —$NR^5$C(=O)$Q^1$ ($R^5$ and $Q^1$ represent the same meanings defined above)}. Examples of the substituent for substituted aryl, substituted aralkyl, substituted heteroaryl and substituted heteroarylalkyl group of $Q^1$ and $Q^2$ include lower alkyl group, halogen atom, trifluoromethyl and cyano group, and the substituents may be plural and the same or different from each other. Further, the lower means that the alkyl part of said group is lower alkyl, and examples of the lower alkyl include the alkyl having 1–4 of the carbon number such as methyl, ethyl, propyl, 2-propyl and butyl.

The saturated cyclic amino groups constituted by 4 to 8 carbons and further optionally one —$NR^8$— ($R^8$ represents the same meaning defined above) or one oxygen atom, which $R^6$ and $R^7$ are combined together to form with the nitrogen atom to which $R^6$ and $R^7$ are bonded, are typically exemplified by 1-pyrrolidinyl, piperidino, 1-homopiperidinyl, morpholino and 4-methylpiperazin-1-yl.

The divalent hydrocarbyl groups having 1–4 of the carbon number for $E^1$ are exemplified by typically straight chain or branched alkylene group, more typically methylene, ethylene, propylene, trimethylene, tetramethylene and 1-ethylethylene.

Examples of the divalent hydrocarbyl group, which may contain unsaturated bond, having 1–6 of the carbon number for $E^2$ include straight chain or branched alkylene group such as methylene, ethylene, trimethylene, tetramethylene and 1-ethylethylene; straight chain or branched alkenylene group such as vinylene, 1-propenylene, 2-butenylene and 4-methyl-2-pentenylene; straight chain or branched alkynylene group such as ethynylene, 2-propynylene, 2-butynylene and 4-methyl-2-pentynylene; and o-, m- and p-phenylene group.

Examples of the substituent for substituted alkyl, substituted alkenyl, substituted alkynyl and substituted cycloalkyl include hydroxy, amino, lower alkylamino, di-lower alkylamino, carboxyl, lower alkoxycarbonyl, benzyloxycarbonyl group, halogen atom, cyano, benzyloxy, alkoxy, lower alkanoyloxy, lower alkylthio, lower alkylsulfinyl, lower alkylsulfonyl, alkanoylamino, lower alkoxycarbonylamino and lower alkylsulfonamido group, herein lower means that the alkyl part of said group is lower alkyl. Such lower alkyl is exemplified by the alkyl group having 1–4 of the carbon number such as methyl, ethyl, propyl, 2-propyl and butyl.

Prodrugs can be exemplified by the compounds reproducing the compound given by formula (1) or (1a). Examples for the compounds having a carboxyl group include the compounds having alkoxycarbonyl, alkylthiocarbonyl or alkylaminocarbonyl group in place of the carboxyl group. Examples for the compounds having an amino group include the compounds having alkanoylamino given by alkanoyl substitution, alkoxycarbonylamino given by alkoxycarbonyl substitution or acyloxymethylamino in place of the amino group, and hydroxylamine compounds. Examples for the compounds having a hydroxy group include the compounds having acyloxy given by acyl substitution, phosphate ester compounds and acyloxymethyoxy compounds. The alkyl part of the group for preparing these prodrugs may be the above-mentioned alkyl group that may be substituted by alkoxy group having 1–6 of the carbon number and so on. Preferable examples for the compound having alkoxycarbonyl in place of carboxyl group include lower (e.g. 1–6 of the carbon number) alkoxycarbonyl such as methoxycarbonyl and ethoxycarbonyl and lower (e.g. 1–6 of the carbon number) alkoxycarbonyl substituted by alkoxy group such as methoxymethoxycarbonyl, ethoxymethoxycarbonyl, 2-methoxyethoxycarbonyl, 2-methoxyethoxymethoxycarbonyl and pivaloylmethoxycarbonyl.

Pharmaceutically acceptable salts can be exemplified by acid addition salts and quarternary ammonium salts.

Examples of the acid for the acid addition salts include inorganic acids such as hydrochloric acid, hydrobromic acid, hydroiodic acid and sulfuric acid, and organic acids such as acetic acid, oxalic acid, citric acid, malic acid, tartaric acid, fumaric acid, maleic acid and methanesulfonic acid.

Examples of the quarternary ammonium salts include the quarternary ammonium salts prepared by the reaction with an alkylating agent of formula:

$$R^9\text{—}G^1$$

(wherein $R^9$ represents lower alkyl group and $G^1$ represents a leaving group), and optionally changing an anion to another physiologically acceptable anion. Preferable lower alkyl groups are exemplified by methyl and ethyl group. Examples of the physiologically acceptable anion include halogen ion, sulfate, phosphate, nitrate, acetate, citrate, fumarate, succinate and so on. Preferable leaving groups are exemplified by chlorine, bromine and iodine atom.

The present compounds have one or more asymmetric carbon atoms and there exist stereoisomers. The present compounds contain a mixture of each isomer and isolated isomer.

The present compounds may be their anhydrides or solvate such as hydrate.

In the present compounds, the compounds wherein the ring W represents benzene or pyridine ring, especially the compounds among them, wherein Z represents formula:

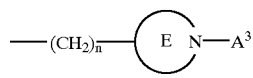

are selective in the muscarinic part of the smooth muscle rather than muscarinic part of the heart. Therefore, they are useful for curing a disease relating to alteration and/or tension of exercise of smooth muscle observed in intestine, trachea and bladder in particular. These diseases include intestinum hypersensitivity, urinary incontinence, pollakiuria, esophageal achalasia and chronic obstructive tracheal disease. Further, among the above-mentioned compounds, the compounds wherein $A^3$ represents cycloalkylmethyl, cycloalkenylmethyl, benzyl or substituted benzyl group are especially useful as pollakiuria and/or urinary incontinence remedy.

When the above-mentioned compounds given by formula (1), their acid addition salts or quarternary ammonium salts are utilized as anticholinergic. medicament, they can be administered parenterally or orally. Namely, liquid formulations such as solution, emulsion and suspension may applied as injections, to which buffer, dissolving assistant, isotonic agent and so on may be optionally added. They can also be administered via rectum as suppository. These formulations are prepared by mixing a usual carrier, excipient, binder, stabilizer and so on with the active ingredient according to general methods. Further, usual preparations such as tablet, capsule, syrup, suspension and so on may be administered orally. The dose and frequency vary depending on the symptom, age, body weight, type of formulation and so on. In case of injecting administration, they may be applied in general, in an amount of 0.1 to 100 mg at once or in several times for adult. They may also be administrated by intravenous drip. In case of oral administration, an amount of 0.1 to 1000 mg, preferably 1 to 400 mg, may be applied once or in several times, for example 2 to 4 times, a day.

In the compounds given by general formula (1), the compound wherein $R^3$ represents hydrogen atom can be prepared by the methods described in U.S. Pat. No. 5,556,860 or their variations. Further, the compound except the compounds wherein $R^3$ represents hydrogen atom can be prepared by the method below:

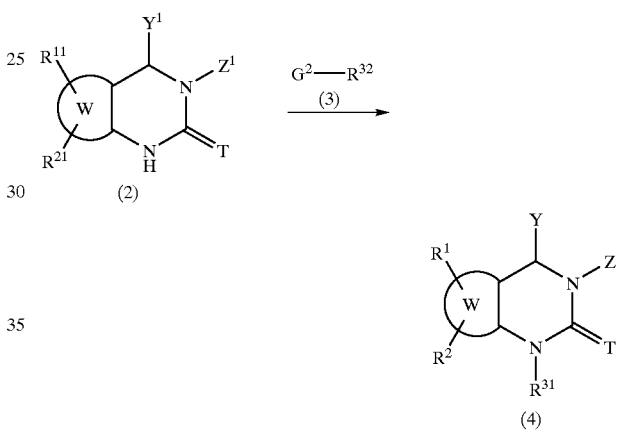

wherein ring W, Y, Z, T, $R^1$ and $R^2$ represent the meanings as defined above. $R^{31}$ means the definition of $R^3$ except hydrogen atom. $Y^1$, $Z^1$, $R^{11}$, $R^{21}$ and $R^{32}$ represent the same groups as Y, Z, $R^1$, $R^2$ and $R^{31}$ respectively, provided that amino, alkylamino, hydroxy, carboxyl and the other reactive groups are protected when these substituents are contained. $G^2$ represents a leaving group.

The compound given by general formula (4) can be prepared by the reaction of the compound given by general formula (2) with an alkylating agent given by general formula (3) in a solvent, and optionally deprotection. The reaction may be usually carried out in a solvent at 0–100° C., preferably room temperature to 70° C. in the presence of a base. Examples of the solvent include ethers such as tetrahydrofuran and dioxane; aromatic hydrocarbons such as benzene and toluene; ketones such as acetone and 2-butanone; and dimethylformamide. Examples of the base include sodium hydride, potassium carbonate, sodium carbonate and triethylamine. In case of utilizing potassium carbonate or sodium carbonate, an addition of sodium iodide or potassium iodide may raise the yield. The leaving group given by $G^2$ is usually halogen atom such as chlorine, bromine and iodine and aromatic sulfonyloxy group such as p-toluenesulfonyloxy group. Examples of the protecting group for amino, alkylamino, hydroxy, carboxyl group and so on include usual protecting groups (e.g. benzyl and acetyl group for protecting hydroxy group, benzyl group for protecting amino group, etc.) used in organic synthesis field in general. These groups can be derived and eliminated by usual methods. (cf. Protective Groups in Organic Synthesis, 2$^{nd}$ ed., John Wiley & Sons, Inc., New York)

EXAMPLES

Hereinafter, the present invention will be explained in detail by preparation examples and test examples, which do not limit the present invention.

Preparation Example 1

Preparation of 3-[1-(Cyclopropylmethyl)piperidin-4-yl]-4-phenyl-3,4-dihydro-2(1H)-quinazolinone

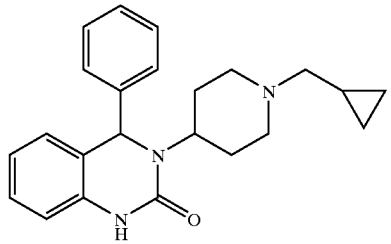

To a solution of 200 mg (0.65 mmol) of 3-(piperidin-4-yl)-4-phenyl-3,4-dihydro-2(1H)-quinazolinone in 5 ml of N,N-dimethylformamide (DMF), 270 mg (1.95 mmol) of potassium carbonate and 176 mg (1.30 mmol) of bromomethylcyclopropane were added at room temperature subsequently and stirred at about 50° C. for 5 hours. The reaction mixture was poured into water, extracted with ethyl acetate, washed with water and saturated brine and dried over anhydrous magnesium sulfate. The solvent was evaporated to afford a residue, which was purified by silica gel column chromatography (chloroform—10% methanol/chloroform) to give 231 mg (0.64 mmol) of the title compound as colorless oil.

To the solution of the above oily product in 15 ml of methanol, 1.0 ml of 1M hydrochloric acid/ether was added and the mixture was concentrated under reduced pressure. To the obtained residue, 30 ml of ether were added, and stirred at room temperature for one hour and under ice-cooling for one hour. The precipitated crystals were collected and recrystallized from isopropanol to give 133 mg of the title compound hydrochloride as colorless crystals. mp 276–281° C.

Preparation Example 2

Preparation of 3-[1-(2-Methylpropyl)piperidin-4-yl]-4-phenyl-3,4-dihydro-2(1H)-quinazolinone In similar way as in Preparation example 1, the title compound hydrochloride was prepared from 3-(piperidin-4-yl)-4-phenyl-3,4-dihydro-2(1H)-quinazolinone and 1-bromo-2-methylpropane. mp 215–225° C.

Preparation Example 3

Preparation of 1-Butyl-3-[1-(Cyclohexylmethyl)piperidin-4-yl]-4-phenyl-3,4-dihydro-2(1H)-quinazolinone

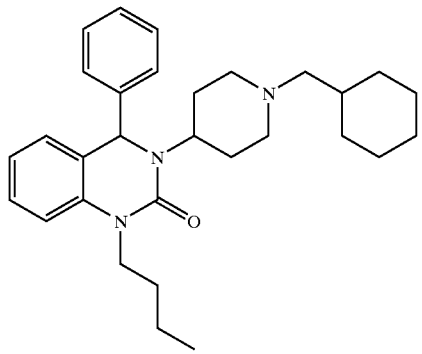

To a solution of 100 mg (0.25 mmol) of 3-[1-(cyclohexylmethyl)piperidin-4-yl]-4-phenyl-3,4-dihydro-2(1H)-quinazolinone in 2 ml of DMF, 22 mg (0.55 mmol) of sodium hydride (60%) were added at room temperature and stirred at about 60° C. for one hour. After allowing the reaction mixture to stand cool, a solution of 69 mg (0.38 mmol) of 1-iodobutane in 1 ml of DMF was added thereto at room temperature and stirred at about 60° C. for 2 hours. The reaction mixture was poured into water, extracted with ethyl acetate, washed with water and saturated brine, and dried over anhydrous magnesium sulfate. After the solvent was evaporated under reduced pressure, the obtained residue was purified by silica gel column chromatography (chloroform—10% methanol/chloroform) to give 88 mg (0.19 mmol) of the title compound as colorless oil.

To the solution of the above oily product in 3 ml of ether, 0.23 ml of 1M hydrochloric acid/ether was added and stirred at room temperature for one hour. Isopropyl ether was added to the solution, followed by stirring at room temperature for one hour and under ice-cooling for one hour. The precipitated crystals were collected to give 78 mg of the title compound hydrochloride as colorless crystals. mp 115–117° C.

The compounds of Preparation examples 4–10 were prepared in similar way as in Preparation example 3.

Preparation Example 4

Preparation of 1-Propyl-3-[1-(cyclohexylmethyl)piperidin-4-yl]-4-phenyl-3,4-dihydro-2(1H)-quinazolinone Hydrochloride mp 135–137° C.

Preparation Example 5

Preparation of 1-Ethyl-3-[1-(cyclohexylmethyl)piperidin-4-yl]-4-phenyl-3,4-dihydro-2(1H)-quinazolinone Hydrochloride mp 137–138° C.

Preparation Example 6

Preparation of 1-Methyl-3-[1-(cyclohexylmethyl)piperidin-4-yl]-4-phenyl-3,4-dihydro-2(1H)-quinazolinone Hydrochloride mp 140–1420° C.

Preparation Example 7

Preparation of 1-Hexyl-3-[1-(cyclohexylmethyl)piperidin-4-yl]-4-phenyl-3,4-dihydro-2(1H)-quinazolinone Hydrochloride mp 60–62° C.

Preparation Example 8

Preparation of 1-(2-Methoxyethyl)-3-[1-(cyclohexylmethyl)piperidin-4-yl]-4-phenyl-3,4-dihydro-2(1H)-quinazolinone Hydrochloride mp 223–225° C.

Preparation Example 9

Preparation of 1-Benzyl-3-[1-(cyclohexylmethyl)piperidin-4-yl] -4-phenyl-3,4-dihydro-2(1H)-quinazolinone Hydrochloride mp 246–248° C.

Preparation Example 10

Preparation of 1-Cyclohexylmethyl-3-[1-(cyclohexylmethyl)piperidin-4-yl]-4-phenyl-3,4-dihydro-2(1H)-quinazolinone Hydrochloride mp 104–106° C.

Preparation Example 11

Preparation of 3-[1-(4-Cyanobenzyl)piperidin-4-yl]-4-phenyl-3,4-dihydro-2(1H)-quinazolinone

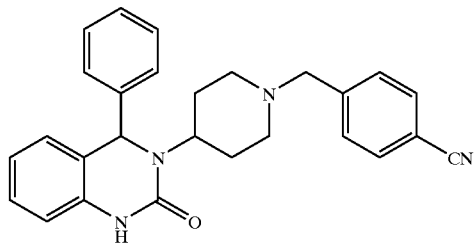

To a solution of 100 mg (0.32 mmol) of 3-(piperidin-4-yl)-4-phenyl-3,4-dihydro-2(1H)-quinazolinone in 3 ml of methanol, 0.08 ml (0.32 mmol) of 4N hydrochloric acid/dioxane, 170 mg (1.3 mmol) of 4-cyanobenzaldehyde, 82 mg (1.3 mmol) of sodium cyanoborohydride were added subsequently under ice-cooling, and stirred at room temperature for 10 hours. Saturated aqueous sodium bicarbonate solution was added to the reaction mixture, followed by extracting with ethyl acetate, washing with water and saturated brine, and drying over anhydrous sodium sulfate. After the solvent was evaporated under reduced pressure, the obtained residue was purified by silica gel column chromatography (chloroform—2% methanol/chloroform) to give the title compound as colorless oil.

To the solution of the above oily product in 2 ml of methylene chloride, 0.6 ml of 1M hydrochloric acid/ether and 1 ml of ethanol were added and stirred. Under a nitrogen atmosphere, ether and methylene chloride were gradually evaporated. The precipitated crystals were collected to give 118 mg of the title compound hydrochloride as colorless crystals. mp 189–192° C.

Preparation Example 12

Preparation of 3-[1-(2-Cyanobenzyl)piperidin-4-yl]-4-phenyl-3,4-dihydro-2(1H)-quinazolinone In similar way as in Preparation example 1, the title compound hydrochloride was prepared from 3-(piperidin-4-yl)-4-phenyl-3,4-dihydro-2(1H)-quinazolinone and α-bromo-2-tolunitrile. mp 220° C. (decomp.)

Preparation Example 13

Preparation of 1-Propyl-3-[1-(3-hydroxymethylbenzyl)piperidin-4-yl]-4-phenyl-3,4-dihydro-2(1H)-quinazolinone

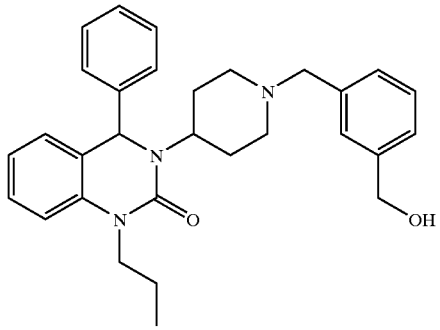

To a solution of 100 mg (0.234 mmol) of 3-[1-(3-hydroxymethylbenzyl) piperidin-4-yl]-4-phenyl-3,4-dihydro-2(1H)-quinazolinone in 2 ml of DMF, 11.2 mg (0.28 mmol) of sodium hydride (60%) were added under ice-cooling and stirred at the same temperature for 5 minutes and at room temperature for 5 minutes. After ice-cooling again, 0.032 ml (0.35 mmol) of 1-bromopropane was added thereto and stirred under ice-cooling for 3 hours and at room temperature for 6 hours. To the reaction mixture, 2 mg of tetrabutylammonium iodide were added and further stirred at room temperature for 5 hours. It was poured into water, extracted with ethyl acetate, washed with water, aqueous saturated sodium bicarbonate solution and saturated brine, and dried over anhydrous sodium sulfate. After the solvent was evaporated under reduced pressure, the obtained residue was purified by silica gel column chromatography (chloroform—2% methanol/chloroform) to give 47 mg (0.10 mmol) of the title compound as colorless oil.

To the solution of the above oily product in 1 ml of ethanol, 0.2 ml of 1M hydrochloric acid/ether was added and the mixture was concentrated under reduced pressure. To the obtained residue, 1 ml of isopropyl alcohol was added and stirred at room temperature for one hour and under ice-cooling for one hour. The precipitated crystals were collected to give 13 mg of the title compound hydrochloride as colorless crystals. mp 108–112° C.

Preparation Example 14

Preparation of 1-(2-Hydroxyethyl)-3-[1-(3-hydroxymethylbenzyl)piperidin-4-yl]-4-phenyl-3,4-dihydro-2(1H)-quinazolinone

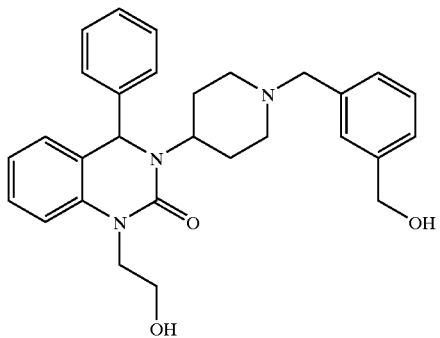

(a) Preparation of 1-(2-tert-Butyldimethylsilyloxyethyl)-3-[1-(3-hydroxymethylbenzyl)piperidin-4-yl]-4-phenyl-3,4-dihydro-2(1H)-quinazolinone To a solution of 200 mg (0.468 mmol) of 3-[1-(3-hydroxymethylbenzyl) piperidin-4-yl]-4-phenyl-3,4-dihydro-2(1H)-quinazolinone in 3 ml of DMF, 22 mg (0.55 mmol) of sodium hydride (60%) were added under ice-cooling and stirred at the same temperature for 5 minutes and at room temperature for 10 minutes. After ice-cooling again, 224 mg (0.55 mmol) of 2-tert-butyldimethylsilyloxyethylbromide and 2 mg of tetrabutylammonium iodide were added thereto and stirred under ice-cooling for 4 hours. It was poured into aqueous sodium bicarbonate solution, extracted with ethyl acetate, washed with water, aqueous saturated sodium bicarbonate solution and saturated brine, and dried over anhydrous sodium sulfate. After the solvent was evaporated under reduced pressure, the obtained residue was purified by silica gel column chromatography (chloroform—3% methanol/chloroform) to give 92 mg (0.16 mmol) of the title compound as colorless oil.

$^1$H NMR(CDCl$_3$); δ 0.04 (6H, s), 0.86 (9H, s), 3.34 (2H, s), 4.39 (1H, m), 4.66 (2H, s), 5.48 (1H, s). 6.92 (1H, dt, J=1 Hz, 7.4 Hz), 7.06–7.31 (13H, m).

(b) Preparation of 1-(2-Hydroxyethyl)-3-[1-(3-hydroxymethylbenzyl)piperidin-4-yl]-4-phenyl-3,4-dihydro-2(1H)-quinazolinone To a solution of the oil obtained by (a) in 2 ml of tetrahydrofuran (THF), 0.31 ml of 1N tetrabutylammonium fluoride/THF solution was added and stirred for 30 minutes at room temperature. Saturated brine was added thereto and the reaction mixture was extracted with ethyl acetate and dried over anhydrous sodium sulfate. After the solvent was evaporated under reduced pressure, the obtained residue was purified by silica gel column chromatography (chloroform—5% methanol/chloroform) to give 63 mg (0.13 mmol) of the title compound as colorless oil.

To the solution of the above oily product in 1 ml of isopropyl alcohol, 12.2 mg (0.13 mmol) of oxalic acid were added, dissolved by heating and stirred at room temperature. The precipitated crystals were collected to give 50 mg of the title compound oxalate as colorless crystals. mp 185–187° C.

Preparation Example 15

Preparation of 3-[1-(3-Methoxymethylbenzyl)piperidin-4-yl]-4-phenyl-3,4-dihydro-2(1H)-quinazolinone In similar way as in Preparation example 11, the title compound hydrochloride was prepared from 3-(piperidin-4-yl)-4-phenyl-3,4-dihydro-2(1H)-quinazolinone and 3-methoxymethylbenzaldehyde. mp 152–157° C.

In similar way as in Preparation example 3, the following compounds were prepared.

Preparation Example 16

1-(3-Cyanopropyl)-3-[1-(cyclohexymethyl)piperidin-4-yl]-4-phenyl-3,4-dihydro-2(1H)-quinazolinone Hydrochloride mp 136–140° C.

Preparation Example 17

1-(2-Methoxyethyl)-3-(1-benzylpiperidin-4-yl)-4-phenyl-3,4-dihydro-2(1H)-quinazolinone $^1$H NMR(CDCl$_3$); δ 2.92 (1H, d, J=11.0 Hz), 3.35 (3H, s), 3.44 (2H, s), 3.65 (2H, t, J=6.5 Hz), 4.00 (1H, dt, J=6.6 Hz, 14.5 Hz), 4.29 (1H, dt, J=6.6 Hz, 14.5 Hz), 4.42 (1H, m), 5.49 (1H, s), 6.96 (2H, t, J=7.7 Hz).

Preparation Example 18

1-(2-Methoxycarbonylethyl)-3-(1-benzylpiperidin-4-yl)-4-phenyl-3,4-dihydro-2(1H)-quinazolinone $^1$H NMR(CDCl$_3$); δ 2.79 (1H, d, J=10.8 Hz), 2.83 (1H, m), 3.44 (2H, s), 3.67 (3H, s), 4.22 (2H, m), 4.41 (1H, m), 5.50 (1H, s), 6.87 (1H, d, J=8.1 Hz), 6.96 (1H, t, J=7.0 Hz).

Preparation Example 19

1-Methoxycarbonylmethyl-3-(1-benzylpiperidin-4-yl)-4-phenyl-3,4-dihydro-2(1H)-quinazolinone $^1$H NMR(CDCl$_3$); δ 2.78 (1H, d, J=11.7 Hz), 2.94 (1H, d, J=11.4 Hz), 3.76 (3H, s), 4.40 (1H, m), 5.55 (1H, s), 6.63 (1H, d, J=8.1 Hz).

Preparation Example 20

1-(3-Cyanopropyl)-3-(1-benzylpiperidin-4-yl)-4-phenyl-3,4-dihydro-2(1H)-qunazolnone $^1$H NMR(CDCl$_3$); δ 2.82 (1H, d, J=11.6 Hz), 2.92 (1H, d, J=10.8 Hz), 3.45 (2H, s), 3,93 (1H, m), 4.14 (1H, m), 4.41 (1H, m), 5.52 (1H, s), 6.85 (1H, t, J=8.2 Hz).

Preparation Example 21

Preparation of 1-(2-Hydroxyethyl)-3-(1-benzylpiperidin-4-yl)-4-phenyl-3,4-dihydro-2(1H)-quinazolinone In similar way as in Preparation example 3, 1-[2-(tetrahydropyran-2-yl)oxyethyl]-3-(1-benzylpiperidin-4-yl)-4-phenyl-3,4-dihydro-2(1H)-quinazolinone was prepared from 99.4 mg (0.25 mmol) of 3-(1-benzylpiperidin-4-yl)-4-phenyl-3,4-dihydro-2(1H)-quinazolinone and 157 mg (0.75 mmol) of 2-(tetrahydropyran-2-yl)oxyethyl bromide as colorless oil. To a solution of the obtained oil in 4 ml of methanol, 57 mg (0.30 mmol) of p-toluenesulfonic acid monohydrate were added and stirred at room temperature for one hour. The reaction liquid was poured into aqueous saturated sodium bicarbonate solution and extracted with ethyl acetate. It was washed with saturated brine and dried over anhydrous sodium sulfate. After the solvent was evaporated under reduced pressure, the obtained residue was purified by silica gel column chromatography (hexane/ethyl acetate, 1/1 to 1/4) to give 100 mg (0.23 mmol) of the title compound as colorless amorphous.

$^1$H NMR(CDCl$_3$); δ 2.74 (1H, d, J=11.0 Hz), 3.41 (2H, s), 3.95 (3H, s), 6.11 (1H, s), 6.64 (1H, d, J=7.9 Hz), 7.37 (2H, dt, J=1.5 Hz, 7.9 Hz).

Preparation Example 22

Preparation of 1-(3-Hydroxypropyl)-3-(1-benzylpiperidin-4-yl)-4-phenyl-3,4-dihydro-2(1H)-quinazolinone In similar way as in Preparation example 21, the title compound was prepared from 3-(1-benzylpiperidin-4-yl)-4-phenyl-3,4-dihydro-2(1H)-quinazolinone and 3-(tetrahydropyran-2-yl)oxypropyl bromide.

$^1$H NMR(CDCl$_3$); δ 2.78 (1H, d, J=11.2 Hz), 2.93 (1H, d, J=7.7 Hz), 3.45 (1H, s), 3.92 (1H, m), 5.53 (1H, s).

Preparation Example 23

Preparation of 1-(3-Aminopropyl)-3-(1-benzylpiperidin-4-yl)-4-phenyl-3,4-dihydro-2(1H)-quinazolinone In similar way as in Preparation example 3, 1-(3-phthalimidopropyl)-3-(1-benzylpiperidin-4-yl)-4-phenyl-3, 4-dihydro-2(1H)-quinazolinone was prepared from 3-(1-benzylpiperidin-4-yl)-4-phenyl-3,4-dihydro-2(1H)-quinazolinone and 3-bromo-1-phthalimidopropane as pale yellow amorphous.

¹H NMR(CDCl₃); δ 2.77 (1H, d, J=11.9 Hz), 2.92 (1H, m), 3.43 (2H, s), 3.80 (2H, t, J=7.0 Hz), 3.93 (1H, m), 4.04 (1H, m), 4.38 (1H, m), 5.49 (1H, s), 6.80 (1H, d, J=7.9 Hz), 7.13–7.27 (12H, m).

To a solution of 96 mg (0.164 mmol) of the above oily product in 2 ml of ethanol, 3.0 ml of 30% methylamine/ethanol solution were added and stirred under reflux-heating for one hour. After the solvent was evaporated under reduced pressure, the obtained residue was purified by silica gel column chromatography (10% methanol/chloroform—20% methanol/chloroform) to give 55 mg (0.12 mmol) of the title compound as colorless amorphous.

¹H NMR(CDCl₃); δ 2.92 (1H, d, J=11.0 Hz), 3.45 (2H, s), 3.95 (1H, m), 4.09 (1H, m), 4.39 (1H, m), 5.51 (1H, s), 6.88 (1H, d, J=8.1 Hz).

Preparation Example 24

Preparation of 1-(2-Carboxyethyl)-3-(1-benzylpiperidin-4-yl)-4-phenyl-3,4-dihydro-2(1H)-quinazolinone To a solution of 78 mg (0.16 mmol) of 1-(2methoxycarbonylethyl)-3-(1-benzylpiperidin-4-yl)-4-phenyl-3,4-dihydro-2(1H)-quinazolinone in 1 ml of methanol, 0.5 ml of 1N aqueous sodium hydroxide solution was added and stirred at room temperature for 2.5 hours. After neutralization with 1N hydrochloric acid, the reaction mixture was concentrated under reduced pressure, extracted with ethyl acetate and dried over anhydrous sodium sulfate. The solvent was evaporated under reduced pressure. Ether was added to the residue and precipitated crystals were collected to give the title compound as colorless powder.

¹H NMR(CDCl₃); δ 2.60–3.10 (4H, m), 3.40 (2H, s), 4.10–4.30 (3H, m), 5.43 (1H, s), 6.79–6.88 (2H, m), 7.00–7.27 (12H, m).

Preparation Example 25

Preparation of 1-Carboxymethyl-3-(1-benzylpiperidin-4-yl)-4-phenyl-3,4-dihydro-2(1H)-quinazolinone In similar way as in Preparation example 24, the title compound was prepared from 1-methoxycarbonylmethyl-3-(benzylpiperidin-4-yl)-4-phenyl-3,4-dihydro-2(1H)-quinazolinone.

¹H NMR(CDCl₃); δ 1.45–1.60 (2H, m), 2.10–2.35 (3H, m), 4.20–4.45 (2H, m), 5.60 (1H, s), 6.79–6.89 (2H, m).

Preparation Example 26

Preparation of 3-(1-Benzylpiperidin-4-yl)-4-(3-methoxyphenyl)-3,4-dihydro-2(1H)-quinazolinone

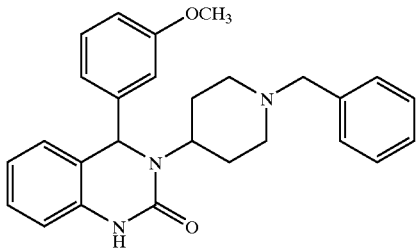

(a) Preparation of 2-Trichloroacetylamino-3'-methoxybenzophenone
To a solution of 2.89 g (12.7 mmol) of 2-amino-3'-methoxybenzophenone and 2.13 ml (15.2 mmol) of triethylamine in 16 ml of tetrahydrofuran (THF), 1.56 ml (14 mmol) of trichloroacetyl chloride were added dropwise under ice-cooling and stirred for 2 hours. Water was added to the reaction mixture, which was followed by extraction with ethyl acetate. The organic layer was washed with saturated brine, dried over anhydrous sodium sulfate and concentrated under reduced pressure. The obtained residue was purified by silica gel column chromatography (hexane/ethyl acetate=15/1) to give 4.51 g (12.1 mmol) of the title compound.
¹H NMR(CDCl₃); δ 3.87 (3H, s), 7.14–7.28 (4H, m), 8.63 (1H, d, J=8.3 Hz).
(b) Preparation of N-(1-Benzylpiperidin-4-yl)-2-trichloroacetylamino-3'-methoxybenzophenoneimine
To a solution of 4.51 g (12.1 mmol) of 2-trichloroacetylamino-3'-methoxybenzophenone in 22 ml of dimethyl sulfoxide (DMSO), 3.70 ml (18.1 mmol) of 4-amino-1-benzylpiperidine were added at room temperature and stirred at about 50° C. for 5 hours. After allowed to stand cool, the reaction mixture was extracted with ethyl acetate, washed with water and saturated brine and dried over anhydrous sodium sulfate. It was concentrated under reduced pressure and the obtained residue was purified by silica gel column chromatography (hexane/ethyl acetate=7/1 to 5/1) to give 4.51 g (7.1 mmol) of the title compound as pale yellow amorphous.
¹H NMR(CDCl₃); δ 1.52–1.59 (2H, m), 1.81 (2H, m), 2.03 (2H, m), 2.84 (2H, m), 3.45 (2H, s), 3.83 (3H, s), 6.72 (1H, d, J=7.5 Hz)
(c) Preparation of α-(2-Aminophenyl)-N-(benzylpiperidin-4-yl)-3-methoxybenzylamine
To a suspension of 3.92 g (7.19 mmol) of N-(1-benzylpiperidin-4-yl)-2-trichloroacetylamino-3'-methoxybenzophenoneimine in 200 ml of methanol, sodium borohydride was added by portions and stirred. After the disappearance of the above starting compound was confirmed, water was added dropwise to the reaction mixture at room temperature and stirred. After concentrated under reduced pressure, the reaction mixture was diluted with ethyl acetate and the organic layer was washed with water and saturated brine and dried over anhydrous sodium sulfate. The liquid was concentrated under reduced pressure and the obtained residue was purified by silica gel column chromatography (hexane/ethyl acetate=4/1 to ethyl acetate) to give 2.65 g (6.6 mmol) of the title compound as colorless oil.
¹H NMR(CDCl₃); δ 3.46 (2H, s), 3.78 (3H, s), 4.73 (1H, brs), 5.05 (1H, s), 6.59–6.65 (2H, m).

(d) Preparation of 3-(1-Benzylpiperidin-4-yl)-4-(3-methoxyphenyl)-3,4-dihydro-2(1H)-quinazolinone To a solution of 2.65 g (6.60 mmol) of α-(2-aminophenyl)-N-(benzylpiperidin-4-yl)-3-methoxybenzylamine in 53 ml of THF, 1.50 g (9.24 mmol) of carbonyldiimidazole were added and stirred under reflux-heating for 3 hours. After allowed to stand cool, the reaction mixture was concentrated under reduced pressure and the obtained residue was purified by silica gel column chromatography (1% methanol/chloroform) to give 2.8 g (6.5 mmol) of the title compound as colorless amorphous.

$^1$H NMR(CDCl$_3$); δ 2.79 (1H, d, J=9.3 Hz), 2.93 (1H, d, J=10.1 Hz), 3.45 (2H, s), 3.75 (3H, s), 4.38 (1H, m), 5.52 (1H, s), 6.66 (1H, d, J=7.7 Hz).

The compounds of Preparation examples 27–36 were prepared in similar way as in Preparation example 26.

Preparation Example 27

Preparation of 3-(1-Benzylpiperidin-4-yl)-4-(4-methoxyphenyl)-3,4-dihydro-2(1H)-quinazolinone $^1$H NMR(CDCl$_3$); δ 1.44–1.62 (3H, m), 1.93–2.12 (3H, m), 2.80 (2H, d, J=10.6 Hz), 2.93 (1H, d, J=8.3 Hz), 3.46 (1H, s), 3.74 (3H, s), 4.35 (1H, m), 5.52 (1H, s), 6.66 (1H, d, J=7.9 Hz), 6.78 (2H, d, J=8.8 Hz)

Preparation Example 28

Preparation of 3-(1-Benzylpiperidin-4-yl)-4-(4-chlorophenyl)-3,4-dihydro-2(1H)-quinazolinone $^1$H NMR(CDCl$_3$); Δ 1.94–2.14 (3H, m), 3.46 (2H, s), 4.39 (1H, m), 5.54 (1H, s), 7.05 (1H, s).

Preparation Example 29

Preparation of 3-(1-Benzylpiperidin-4-yl)-4-(3-chlorophenyl)-3,4-dihydro-2(1H)-quinazolinone $^1$H NMR(CDCl$_3$); δ 2.93 (1H, d, J=11.1 Hz), 3.46 (2H, s), 4.42 (1H, m), 5.54 (1H, m), 6.69 (1H, d, J=7.7 Hz).

Preparation Example 30

Preparation of 3-(1-Benzylpiperidin-4-yl)-4-phenyl-6-methoxy-3,4-dihydro-2(1H)-quinazolinone $^1$H NMR(CDCl$_3$); δ 1.40–1.65 (3H, m), 1.90–2.20 (3H, m), 2.75–2.95 (2H, m), 3.44 (2H, s), 3.72 (3H, s), 5.50 (1H, s), 6.59 (1H, d, J=8.6 Hz).

Preparation Example 31

Preparation of 3-(1-Benzylpiperidin-4-yl)-4-(2-methoxyphenyl)-3,4-dihydro-2(1H)-quinazolinone $^1$H NMR(CDCl$_3$); δ 1.92–2.13 (3H, m), 2.76 (1H, d, J=11.2 Hz), 2.93 (1H, d, J=10.3 Hz), 3.45 (2H, s), 3.95 (3H, s), 4.35 (1H, m), 6.11 (1H, s), 6.64 (1H, d, J=7.7 Hz).

Preparation Example 32

Preparation of 3-(1-Benzylpiperidin-4-yl)-4-(4-fluorophenyl)-3,4-dihydro-2(1H)-quinazolinone $^1$H NMR(CDCl$_3$); δ 1.38–1.72 (3H, m), 1.80–2.15 (3H, m), 2.77–3.00 (2H, m), 3.46 (2H, s), 4.38 (1H, m), 5.55 (1H, s), 6.70 (1H, d, J=8.4 Hz), 6.88–6.97 (3H, m), 7.15(2H, m), 7.21–7.37 (8H, m).

Preparation Example 33

Preparation of 3-(1-Benzylpiperidin-4-yl)-4-(3-fluorophenyl)-3,4-dihydro-2(1H)-quinazolinone $^1$H NMR(CDCl$_3$); δ 1.40–1.76 (3H, m), 3.46 (2H, s), 4.42 (1H, m), 5.55 (1H, s), 6.73 (1H, d, J=8.0 Hz), 6.85–6.99 (2H, m), 7.60 (1H, s).

Preparation Example 34

Preparation of 3-(1-Benzylpiperidin-4-yl)-4-(2-fluorophenyl)-3,4-dihydro-2(1H)-quinazolinone $^1$H NMR(CDCl$_3$); δ 1.40–1.76 (3H, m), 3.46 (2H, s), 4.38 (1H, m), 6.00 (1H, s), 6.69 (1H, d, J=7.0 Hz), 6.88–7.32 (12H, m).

Preparation Example 35

Preparation of 3-(1-Benzylpiperidin-4-yl)-4-phenyl-7-chloro-3,4-dihydro-2(1H)-quinazolinone

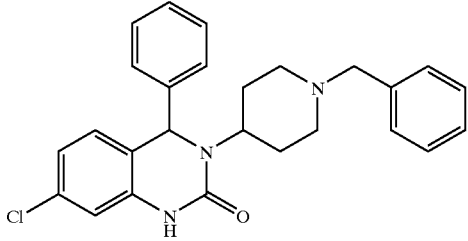

$^1$H NMR(CDCl$_3$); δ 2.76–2.94 (2H, m), 3.44 (2H, s), 4.30–4.42 (1H, m), 5.52 (1H, s), 6.68 (1H, d, J=2.0 Hz), 6.86 (1H, dd, J=2.0 Hz, 8.1 Hz), 7.05–7.08 (2H, m).

Preparation Example 36

Preparation of 3-(1-Benzylpiperidin-4-yl)-4-phenyl-6-fluoro-3,4-dihydro-2(1H)-quinazolinone $^1$H NMR(CDCl$_3$); δ 2.76–2.94 (2H, m), 3.45 (2H, s), 4.30–4.44 (1H, m), 5.50 (1H, s), 6.62 (1H, dd, J=4.6 Hz, 8.6 Hz), 7.04 (1H, br).

Preparation Example 37

Preparation of 3-[1-(3-Methoxymethybenzyl)piperidin-4-yl]-4-(3-methoxy)phenyl-3,4-dihydro-2(1H)-quinazolinone (a) Preparation of 3-(Piperidin-4-yl)-4-(3-methoxy)phenyl-3,4-dihydro-2(1H)-quinazolinone To a solution of 2.48 g (5.81 mmol) of 3-(1-benzylpiperidin-4-yl)-4-(3-methoxy)phenyl-3,4-dihydro-2(1H)-quinazolinone in 50 ml of methanol, 1.46 g (23.2 mmol) of ammonium formate and 125 mg of 10% palladium/carbon were added and stirred under reflux-heating for one hour. Further, 1.46 g (23.2 mmol) of ammonium formate and 125 mg of 10% palladium/carbon were added and stirred under reflux-heating for additional one hour. After allowed to stand cool, the reaction mixture was subjected to celite filtration and the filtrate was concentrated under reduced pressure. The residue was dissolved with chloroform, washed with dilute aqueous ammonia and saturated brine, subsequently, dried over anhydrous sodium sulfate and concentrated under reduced pressure. Precipitated crystals from isopropanol were collected to give 1.69 g (5.01 mmol) of the title compound as colorless crystal.

$^1$H NMR(CDCl$_3$); δ 3.87 (3H, s), 7.14–7.28 (4H, m), 8.63 (1H, d, J=8.3 Hz); $^1$H NMR(CDCl$_3$); δ 1.55–1.67 (3H, m), 2.54–2.74 (2H, m), 2.98 (1H, dd, J=1.8 Hz, 10.4 Hz), 3.12 (1H, dd, J=1.5 Hz, 13.8 Hz), 3.76 (3H, s), 4.40 (1H, m), 5.52 (1H, s), 6.68 (1H, d, J=7.9 Hz).

(b) Preparation of 3-[1-(3-Methoxymethylbenzyl)piperidin-4-yl]-4-(3-methoxy)phenyl-3,4-dihydro-2(1H)-quinazolinone In similar way as in Preparation example 11, the title compound was prepared from 3-(piperidin-4-yl)-4-(3-methoxy)phenyl-3,4-dihydro-2(1H)-quinazoline and 3-methoxymethylbenzaldehyde.

$^1$H NMR(CDCl$_3$); δ 2.79 (1H, d, J=11.7 Hz), 2.93 (1H, d, J=8.4 Hz), 3.39 (3H, s), 3.45 (2H, s), 3.75 (3H, s), 4.37 (1H, m), 4.44 (2H, s), 5.52 (1H, s), 6.66 (1H, d, J=7.9 Hz), 6.71 (1H, dd, J=1.6 Hz, 8.2 Hz).

The compounds of Preparation examples 38–41 were prepared in similar way as in Preparation example 37.

Preparation Example 38

Preparation of 3-[1-(3-Methoxymethylbenzyl) piperidin-4-yl]-4-(4-methoxy)phenyl-3,4-dihydro-2 (1H)-quinazolinone $^1$H NMR(CDCl$_3$); δ 1.97–2.12 (3H, m), 3.45 (2H, s), 3.74 (3H, s), 4.34 (1H, m), 4.44 (2H, s), 5.51 (1H, s), 6.65 (1H, d, J=7.7 Hz), 6.76–6.80 (3H, m).

Preparation Example 39

Preparation of 3-[1-(3-Methoxymethylbenzyl) piperidin-4-yl]-4-(4-fluoro)phenyl-3,4-dihydro-2 (1H)-quinazolinone $^1$H NMR(CDCl$_3$); δ 1.90–2.13 (3H, m), 2.76–2.99 (2H, m), 3.39 (3H, s), 3.46 (2H, s), 4.37 (1H, m), 4.44 (2H, s), 5.55 (1H, s), 6.70 (1H, d, J=7.2 Hz), 7.46 (1H, s).

Preparation Example 40

Preparation of 3-[1-(3-Methoxymethylbenzyl) piperidin-4-yl]-4-(3-fluoro)phenyl-3,4-dihydro-2 (1H)-quinazolinone $^1$H NMR(CDCl$_3$); δ 2.75–2.99 (2H, m), 3.38 (3H, s), 3.46 (2H, s), 4.43 (1H, m), 4.44 (2, H, s), 5.55 (1H, s), 6.75 (1H, d, J=7.9 Hz), 8.02 (1H, s).

Preparation Example 41

Preparation of 3-[1-(3-Methoxymethylbenzyl) piperidin-4-yl]-4-(2-fluoro)phenyl-3,4-dihydro-2 (1H) -quinazolinone $^1$H NMR(CDCl$^3$); δ 2.77–2.96 (2H, m), 3.39 (3H, s), 3.47 (2H, s), 4.40 (1H, m), 4.44 (2H, s), 6.00 (1H, s), 6.71 (1H, d, J=7.7 Hz), 6.98–7.05 (2H, m), 7.44–7.51 (2H, m).

Preparation Example 42

Preparation of 3-[1-(3-Methoxymethylbenzyl) piperidin-4-yl]-4-(4-chlorophenyl)-3,4-dihydro-2 (1H)-quinazolinone

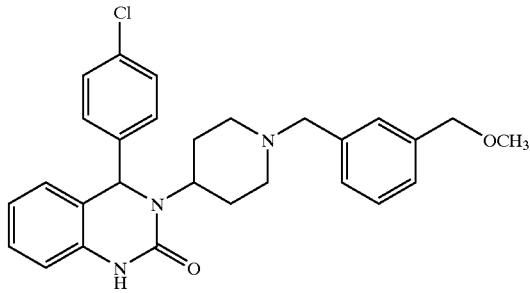

(a) Preparation of 3-(Piperidin-4-yl)-4-(4-chlorophenyl)-3, 4-dihydro-2(1H)-quinazolinone To a solution of 1.40 g (3.25 mmol) of 3-(1-benzylpiperidin-4-yl)-4-(4-chlorophenyl)-3,4-dihydro-2 (1H)-quinazolinone in methylene chloride, α-chloroethyl chloroformate was added dropwise under ice-cooling and stirred for one hour. After concentration under reduced pressure, the residue was dissolved with 28 ml of methanol and stirred at room temperature for 2 hours and under ice-cooling for one hour. The precipitated crystals were collected to give 1.08 g (3.16 mmol) of the title compound as colorless crystal.

$^1$H NMR(CDCl$_3$); δ 3.16–3.38 (2H, m), 4.19 (1H, m), 5.68 (1H, s), 6.80–6.88 (2H, m), 7.24 (1H, d, J=7.3 Hz).

(b) Preparation of 3-[1-(3-Methoxymethylbenzyl)piperidin-4-yl]-4-(4-chlorophenyl)-3,4-dihydro-2(1H)-quinazolinone In similar way as in Preparation example 11, the title compound was prepared from 3-(piperidin-4-yl)-4-(4-chlorophenyl)-3,4-dihydro-2(1H)-quinazolinone and 3-methoxymethylbenzaldehyde.

$^1$H NMR(CDCl$_3$); δ 2.80 (1H, d, J=13.2 Hz), 2.93 (1H, d, J=10.1 Hz), 3.39 (3H, s), 3.46 (2H, s), 4.38 (1H, m), 4.44 (2H, s), 5.54 (1H, s), 6.68 (1H, d, J=7.9 Hz), 7.01–7.16 (3H, m).

The compound of Preparation example 43 was prepared in similar way as in Preparation example 42.

Preparation Example 43

Preparation of 3-[1-(3-Methoxymethylbenzyl) piperidin-4-yl]-4-(3-chlorophenyl)-3,4-dihydro-2 (1H)-quinazolinone $^1$H NMR(CDCl$_3$); δ 1.95–2.18 (3H, m), 2.93 (1H, d, J=10.6 Hz), 3.39 (3H, s), 3.46 (2H, s), 4.40 (1H, m), 5.54 (1H, s), 6.68 (1H, d, J=7.9 Hz), 6.96 (1H, s), 7.11–7.36 (10H, m).

The compounds of Preparation examples 44 and 45 were prepared in similar way as in Preparation example 42(a) and Preparation example 1.

Preparation Example 44

Preparation of 3-[1-(3-Methoxymethylbenzyl) piperidin-4-yl]-4-phenyl-6-chloro-3,4-dihydro-2 (1H)-quinazolinone $^1$H NMR(CDCl$_3$); δ 2.75–2.94 (2H, m), 3.38 (3H, s), 3.45 (2H, s), 4.28–4.41 (1H, m), 4.43 (2H, s), 5.50 (1H, s), 6.63 (1H, d, J=8.3 Hz), 7.07 (1H, dd, J=2.2 Hz, 8.4 Hz), 7.13 (1H, d, J=2.2 Hz).

Preparation Example 45

Preparation of 3-[1-(3-Methoxymethylbenzyl)piperidin-4-yl]-4-phenyl-7-chloro-3,4-dihydro-2(1H)-quinazolinone $^1$H NMR(CDCl$_3$); δ 2.76–2.94 (2H, m), 3.38 (3H, s), 3.45 (2H, s), 4.37–4.46 (3H, m), 5.52 (1H, s), 6.75 (1H, d, J=1.8 Hz), 6.85 (1H, dd, J=1.8 Hz, 8.3 Hz), 7.06 (1H, d, J=8.3 Hz).

Test Example

Antagonism effect on muscarinic receptor of the compounds described in the present specification was measured.

The tests were performed generally according to the methods by T. Yamamoto, et al (Drug Development Research, 34, 9–18, 1995), L. Noronha-Blob et al (J. pharmacol. Exp. Ther., 256, 562–567, 1991) and M. Eltze et al (Eur. J. Pharmacol., 151, 205–211,1988). Namely, urinary bladder and atrium cordis were isolated from Hartley strain male guinea pig (310–750 g) and vas deferens was isolated from New Zealand white male rabbit (2.2–2.6 kg). Urinary bladder, right atrium and vas deferens were suspended with a Krebs-Henseleit solution in organ bath at 31° C. (37° C. in case of urinary bladder) and mixed gas (95% of O$_2$ and 5% of CO$_2$) was insufflated. One side was fixed at a support device and the other side was connected with an isometric transducer. To the specimen, 0.5 to 1.0 g of resting tension (1.0 g in case of urinary bladder and 0.75 g in case of vas deferens) was charged in advance and stabilized. The tension change of the urinary bladder, right atrium and vas deferens was given by a recorder. In the case of vas deferens, the twitch contractions induced by electrical stimulation (condition: 0.05 Hz, 20V, 0.5 ms) was obtained in Krebs-Henseleit solution containing 1 μM of yohimbine hydrochloride.

Acetylcholine (urinary bladder), carbachol (atrium cordis) and McN-A343 (vas deferens) were applied into the organ bath until a maximum reaction, accumulatively. After discarding the Krebs-Henseleit solution in the organ bath, a Krebs-Henseleit solution containing a test compound in low concentration was filled again, treated for 30 minutes and then the cholinergic agents were accumulatively applied into the organ bath. In similar way, the test compounds in higher concentration were treated and the above procedures were repeated. Each of the organs was evaluated respectively at two to three concentrations of test compounds.

The reaction ratio in the presence of the test compounds was calculated as a percentage of the maximum reaction elicited by the cholinergic agents without test compounds. After plotting a concentration-reaction curve, pA$_2$ (the negative logarithm of the concentrations of the test compounds for parallel shifting the concentration-reaction curve of the cholinergic agents to double the concentration) was calculated (Shiro MORIMOTO, Yakurigaku-Jisshusho published by Hirokawa-Shoten).

The results were shown in Table 1.

Test compound 1: 3-[1-(cyclohexylmethyl)piperidin-4-yl]-4-phenyl-3,4-dihydro-2(1H)-quinazolinone hydrochloride Test compound 2: 3-[1-(3-carbamoylbenzyl)piperidin-4-yl]-4-phenyl-3,4-dihydro-2(1H)-quinazolinone hydrochloride Test compound 3: 3-[1-(3-methoxymethylbenzyl)piperidin-4-yl]-4-phenyl-3,4-dihydro-2(1H)-quinazolinone Test compound 4: 3-[1-[(3-cyclohexen-1-yl)methyl]piperidin-4-yl]-4-phenyl-3,4-dihydro-2(1H)-quinazolinone hydrochloride Test compound 5: 3-(1-benzylpiperidin-4-yl)-4-(2-fluorophenyl)-3,4-dihydro-2(1H)-quinazolinone hydrochloride Test compound 6: 3-(1-benzylpiperidin-4-yl)-4-(3-methoxyphenyl)-3,4-dihydro-2(1H)-quinazolinone hydrochloride Test compound 7: 3-(1-benzylpiperidin-4-yl)-4-phenyl-7-chloro-3,4-dihydro-2(1H)-quinazolinone hydrochloride

TABLE 1

| Test compounds | pA$_2$ value | | |
|---|---|---|---|
| | M1(seminiferous duct) | M2(atrium cordis) | M3(urinary bladder) |
| 1 | <6 | <6 | 7.90 |
| 2 | 7.37 | 6.71 | 8.58 |
| 3 | 7.13 | 6.85 | 8.44 |
| 4 | 7.39 | 6.43 | 7.93 |
| 5 | 7.1 | 6.4 | 8.5 |
| 6 | 7.2 | 6.5 | 8.4 |
| 7 | 6.5 | 6.1 | 7.9 |

Industrial Availability

The present compounds have antagonism effect on muscarinic receptor and can be used for anticholinergic medicaments. Therefore, they can be used, for example, as mydriatic medicament, anticonvulsant, parkinsonian remedy, antasthmatic, peptic ulcer remedy, secretagogue and motofacient for gastric and duodenal ulcer, intestinum hypersensitivity remedy, pollakiuria remedy, urinary incontinence remedy, antiarrhythmic medicament, esophageal achalasia remedy, chronic obstructive tracheal disease remedy and so on.

What is claimed is:

1. A method for treating urinary incontinence or pollakiuria, which comprises administering a compound given by general formula (1):

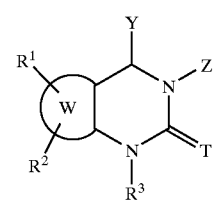

(1)

[wherein T represents oxygen or sulfur atom, and Y represents alkyl, cycloalkyl, cycloalkylalkyl, phenyl, substituted phenyl, aralkyl, substituted aralkyl, heteroaryl or substituted heteroaryl group; ring W represents benzene, a 5–10 membered cycloalkene or a 5–10 membered cycloalkane ring; R$^1$ and R$^2$ represent independently hydrogen atom, lower alkyl group, halogen atom, cyano, trifluoromethyl, nitro, amino, substituted amino, hydroxy, lower alkoxy, lower alkylthio, lower alkylsulfinyl or lower alkylsulfonyl group; R$^3$ represents hydrogen atom, alkyl, substituted alkyl, alkenyl, substituted alkenyl, alkynyl, substituted alkynyl, cycloalkyl, substituted cycloalkyl, cycloalkylalkyl, aralkyl or substituted aralkyl group;

Z represents a group given by formula (1a) or (1b):

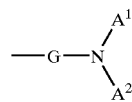
(1a)

{wherein $A^1$ and $A^2$ represent independently hydrogen atom, alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —$CH_2R^4$ group (wherein $R^4$ represents alkenyl or alkynyl group), or $A^1$ and $A^2$ are combined together and form heterocyclic ring; G represents straight chain alkylene having 1–6 of the carbon number, branched alkylene having 2–8 of the carbon number, a group given by formula:

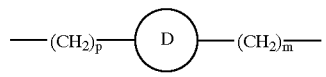

(wherein p and m represent independently 0, 1 or 2 and D represents cycloalkane ring)} or

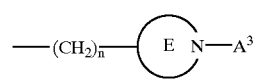
(1b)

{wherein n represents 0, 1 or 2, ring E represents 4–8 membered saturated heterocyclic ring containing nitrogen atom(s), and $A^3$ represents hydrogen atom, alkyl, substituted alkyl, cycloalkyl, saturated heterocyclic, cycloalkylalkyl, cycloalkenylalkyl, aralkyl, substituted aralkyl, heteroarylalkyl, substituted heteroarylalkyl or —$CH_2R^4$ group (wherein $R^4$ represents alkenyl or alkynyl group), or forms bicyclo ring together with ring E}], or pharmaceutically acceptable salt to a subject in need thereof.

2. The method according to claim 1, wherein ring W represents a 5–10 membered cycloalkene or a 5–10 membered cycloalkane ring.

3. The method according to claim 1, wherein ring W represents a benzene ring and Z represents a group given by formula:

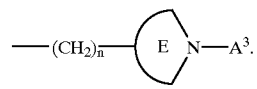
(1b)

4. The method according to claim 1, wherein Z represents a group given by formula:

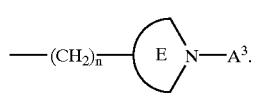
(1b)

5. The method according to claim 4, wherein ring W represents a benzene ring and wherein Y represents a phenyl or a substituted phenyl group.

6. The method according to claim 1, wherein ring W represents a benzene ring and Z represents a group (1b) wherein n represents 0, E represents a 6 membered saturated heterocyclic ring containing a nitrogen atom, given by formula:

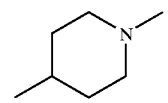

and $A^3$ represents a substituted alkyl given by formula: $CH_2$—$A^4$ (wherein $A^4$ represents a phenyl, a substituted phenyl, a cycloalkyl or a cycloalkenyl group).

7. The method according to claim 6, wherein $A^4$ represents a cycloalkyl or a cycloalkenyl group.

8. The method according to claim 6, wherein $A^4$ represents a phenyl or a substituted phenyl group.

9. The method according to claims 6, wherein $A^4$ represents substituted phenyl group and said substituent is cyano, alkoxyalkyl, alkanoylamino, aminocarbonyl, alkylaminocarbonyl or dialkylaminocarbonyl group.

10. The method according to claim 1, wherein T represents an oxygen atom, Y represents a phenyl group; ring W represents a benzene ring; $R^1$, $R^2$ and $R^3$ represent a hydrogen atom; and Z represents a group (1b) wherein n represents 0, E represents a 6 membered saturated heterocyclic ring containing a nitrogen atom, given by formula:

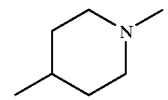

and $A^3$ represents a substituted alkyl given by formula: $CH_2$—$A^4$ (wherein $A^4$ represents a substituted phenyl group).

* * * * *